(12) United States Patent
Roots et al.

(10) Patent No.: US 9,867,562 B2
(45) Date of Patent: Jan. 16, 2018

(54) VECTOR SPACE METHODS TOWARDS THE ASSESSMENT AND IMPROVEMENT OF NEUROLOGICAL CONDITIONS

(71) Applicants: Kurt Roots, Minneapolis, MN (US); Monika Drummond Roots, Minneapolis, MN (US); Jaideep Srivastava, Plymouth, MN (US); Sanjana Srivastava, Playmouth, MN (US)

(72) Inventors: Kurt Roots, Minneapolis, MN (US); Monika Drummond Roots, Minneapolis, MN (US); Jaideep Srivastava, Plymouth, MN (US); Sanjana Srivastava, Playmouth, MN (US)

(73) Assignee: Teladoc, Inc., Purchase, NY (US)

( * ) Notice: Subject to any disclaimer, the term of this patent is extended or adjusted under 35 U.S.C. 154(b) by 402 days.

(21) Appl. No.: 14/734,800

(22) Filed: Jun. 9, 2015

(65) Prior Publication Data
US 2015/0305663 A1    Oct. 29, 2015

Related U.S. Application Data

(63) Continuation-in-part of application No. 14/064,094, filed on Oct. 25, 2013, now Pat. No. 9,324,241, which is a continuation-in-part of application No. 13/657,332, filed on Oct. 22, 2012, now Pat. No. 9,014,614.

(60) Provisional application No. 62/101,300, filed on Jan. 8, 2015, provisional application No. 61/719,280, filed on Oct. 26, 2012, provisional application No. 61/549,698, filed on Oct. 20, 2011, provisional application No. 61/551,384, filed on Oct. 25, 2011.

(51) Int. Cl.
*G09B 19/00* (2006.01)
*A61B 5/16* (2006.01)
*G09B 5/06* (2006.01)
*G09B 23/28* (2006.01)

(52) U.S. Cl.
CPC .............. *A61B 5/168* (2013.01); *A61B 5/162* (2013.01); *G09B 5/06* (2013.01); *G09B 19/00* (2013.01); *G09B 23/28* (2013.01)

(58) Field of Classification Search
CPC ........... A61B 5/168; A61B 5/162; A61B 5/16; A61B 5/165; A61B 5/6896; G09B 19/00; G09B 23/28; G06T 19/345
See application file for complete search history.

(56) References Cited

U.S. PATENT DOCUMENTS

2012/0258436 A1    10/2012    Lee

FOREIGN PATENT DOCUMENTS

JP    2003108529 A    4/2003

OTHER PUBLICATIONS

The Office Action issued by Japanese Patent Office dated Jun. 30, 2017 for the corresponding Japanese patent application No. 2015-539695.

*Primary Examiner* — Robert J Utama
*Assistant Examiner* — Jerry-Daryl Fletcher
(74) *Attorney, Agent, or Firm* — Edward P. Heller, III

(57) ABSTRACT

Path variables of a mallet cube until a hit in an interactive game involving cubes movable in three dimensions are indicative of both hyperactivity and inattention.

11 Claims, 7 Drawing Sheets

VECTOR SPACE METHODS TOWARDS THE ASSESSMENT AND IMPROVEMENT OF NEUROLOGICAL CONDITIONS

RELATED APPLICATIONS

The present application is a nonprovisional of U.S. provisional application No. 62/101,300, filed Jun. 10, 2014; and is a continuation-in-part of U.S. patent application Ser. No. 14/064,094, filed Oct. 25, 2013, which is a nonprovisional of U.S. provisional application No. 61/719,280, filed Oct. 26, 2012; and is a continuation-in-part of U.S. patent application Ser. No. 13/657,332, filed Oct. 22, 2012, which claims the benefit of provisional application Ser. No. 61/549,698, filed Oct. 20, 2011, and Ser. No. 61/551,384, filed Oct. 25, 2011; the contents of which are hereby incorporated by reference in their entirety.

BACKGROUND OF THE INVENTION

1. Field of the Invention

The invention relates to the field of cognitive disorders including assessing attention deficits and/or comorbidities, treating attention deficit hyperactivity disorder, and/or conditions with attentional impairment such as autism spectrum disorder (ASD), anxiety, depression, and Alzheimer's.

2. Background of the Art

Based on the National Survey of Children's Health, 5.4 million children, 4-17 years of age, met criteria for attention deficit hyperactivity disorder (ADHD) in 2007.1 Despite this high number, only 50 percent of children and adolescents are estimated to be diagnosed and treated. A core deficit in ADHD is impairment in executive functioning. Significant debate about the causes and pathophysiology associated with its development persists. Studies investigating the neurochemistry, neuroimaging, and neuropsychological genetics have found evidence suggesting that frontal/striatal regions playa key role in the pathophysiology of executive functioning disorders, namely, the caudate, putamen, lateral prefrontal cortex, and dorsal anterior cingulate cortex. Abnormal structure, functioning, or both of these regions have been implicated in ADHD, 4 further linked to abnormal functioning of norepinephrine and dopamine systems, which affects working memory. Working memory is the capacity to hold in mind information that is used to guide behavior, and deficits in this regard have been proposed to underlie inattention, distractibility, and poor academic performance identified in ADHD.

Current diagnostic tools used to identify executive functioning deficits and child behavior problems are subjective, such as the Conners' Rating Scales, and can thus produce variable clinical impressions. The Continuous Performance Test (CPT) is objective, but has not proved to be a reliable means to identify ADHD. The gold standard of diagnosis remains a professional psychiatric evaluation, which unfortunately is a limited resource in the United States and worldwide.

A rapidly growing field called "Games-With-a-Purpose" has been successful in solving several serious scientific problems. Tangible user interfaces are a novel and useful medium for games meant to aid in diagnosis of behavioral disorders. Differing from traditional graphical user interfaces, tangible user interfaces allow participants to have more naturalistic interaction with presented information and experience through physically holding and moving the devices representing game objects and interact with games. This is an important advancement from the traditional use of simple button press responding. Furthermore, this technology introduces vastly more measurement opportunities not available with a graphical user interface (i.e., button presses). Precise movement can be detected, which is especially useful for examining executive functioning-based disorders that bear on motor behaviors such as hyperactivity involving excessive movement, while inattention leads to delays and increased variability in response to stimulation.

SUMMARY OF THE INVENTION

In an effort to aid diagnosis in schools and medical provider offices, the invention provides a new approach for identification of executive functioning deficits using quantitative data of subjects' actual behavior, eliminating human-made subjective observation. The data are collected in a game ("Groundskeeper"; CogCubed Inc., Minneapolis, Minn.) that is designed to stimulate and entertain the subject.

"Groundskeeper" engages participants through a tangible platform with interesting images, sounds, and challenges to motivate the child. The inventors have developed models to predict executive functioning disorders, with data collected from test subjects' gameplay using a machine learning approach. Machine learning is a branch of artificial intelligence that focuses on developing and utilizing algorithms to process data that automatically identifies patterns in data that model latent real-world relationships using multiple techniques, including supervised learning.

Such game-based objective measurement approaches can bear several important advantages, such as (1) they are highly engaging, allowing investigators to consider potentially confounding effects of boredom, (2) they are objective, (3) they provide more dimensions by which behavior data can be captured (see below), (4) they provide more ecologically valid assessment conditions, and (5) they are limited to a finite period of time and are not staff-intensive to administer, making it more accessible.

Such assessment technologies will play important future role as diagnostic aids by improving psychiatric diagnostic fidelity and making diagnostic aids more accessible for earlier identification and treatment. To this end, the present invention employs the machine learning-based clinical assessment protocol as a diagnostic aid for ADHD.

DETAILED DESCRIPTION

Subjects were children and adolescents between 6 and 17 years of age (n=52) as indicated in Table 1. They were recruited from two outpatient clinics. Twenty-six subjects were included in the study who met diagnostic criteria for ADHD, along with 26 age- and sex-matched comparison subjects without ADHD (Table 1). The study participants were administered the Schedule for Affective Disorders and years of age (n=52) as indicated in Table 1. They were recruited from two outpatient clinics. Twenty-six subjects were included in the study who met diagnostic criteria for ADHD, along with 26 age- and sex-matched comparison subjects without ADHD (Table 1). The study participants were administered the Schedule for Affective Disorders and Schizophrenia for School-Age Children-Present and Lifetime Version, a semistructured diagnostic interview conducted by a psychiatric nurse trained by a child/adolescent psychiatrist at a community-based clinic (j=1.0) and reviewed by two independent child/adolescent psychiatrists. Participants were eligible to participate if they met criteria for ADHD, depressive disorder, anxiety disorders, oppositional defiant disorder, panic disorder, or eating disorders. Across groups, subjects were excluded if they had a history of psychosis, IQ of 55 and below, chemical use disorders, conduct disorder, tic disorders, or any physical ailment that would impede gameplay with the Sifteo Cubes (Sifteo, Inc., San Francisco, Calif.) game system (small tangible computers). Stimulant medications for ADHD were withheld on the day of testing.

The procedures followed were in accordance with the ethical standards of the responsible committee on human experimentation (institutional and national) and with the Helsinki Declaration of 1975, as revised in 2008.

TABLE 1

DEMOGRAPHIC CHARACTERISTICS OF STUDY SUBJECTS

| | Number (percentage of total) | |
|---|---|---|
| Characteristic | ADHD (n = 26) | No ADHD (n = 26) |
| Age (years) (mean) | 12.6 | 14.7 |
| Gender | | |
| Male | 16 (62) | 10 (38) |
| Female | 10 (38) | 16 (62) |
| Race | | |
| White | 17 (65) | 23 (88) |
| Black/African American | 6 (23) | 2 (8) |
| Hispanic | 1 (4) | 0 (0) |
| Other | 2 (8) | 1 (4) |
| Diagnoses | | |
| ADHD with inattentive symptoms | 26 (100) | |
| ADHD with both inattentive and hyperactive symptoms | 17 (65) | |
| Comorbidities | | |
| Depressive disorders | 9 (35) | 16 (62) |
| Anxiety disorders | 18 (69) | 24 (92) |
| Autism spectrum disorders | 9 (35) | 4 (15) |
| Disruptive behavior disorders | 10 (38) | 3 (12) |

ADHD, attention deficit hyperactivity disorder.

The Game

Figure 1:
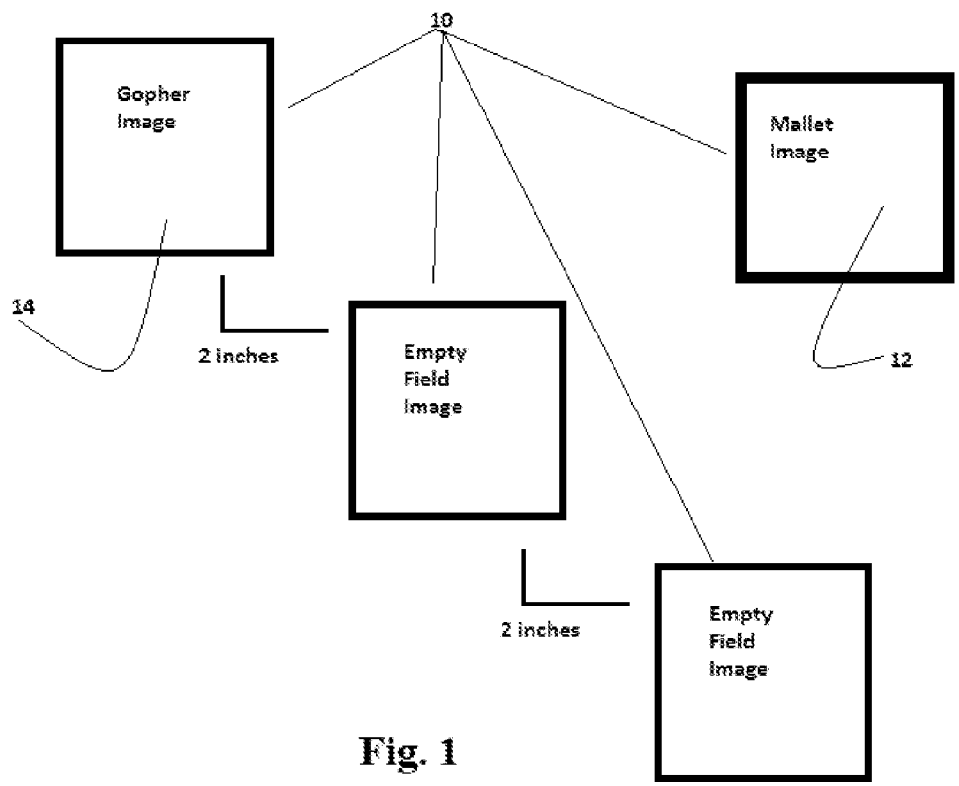
FIG. 1 illustrates a plurality of tangible-graphical interactive cubes.

The invention employs game called "Groundskeeper," using the Sifteo Cubes gaming platform, for aiding in the diagnosis of ADHD. The Sifteo Cubes are based on the principle of tangible user interfaces. They have screens on one side and are used through motion (shaking, tilting, pressing, etc.). The Cubes communicate wirelessly and can be synced to a computer that runs the game and collects data. As shown in FIG. 1, "Groundskeeper" is played using the Sifteo Cubes 10 and a placement board (not shown). One Cube 12 is always used as a "mallet" to hit game targets. Initially, three Cubes are placed in a straight vertical line. Each of these three Cubes has an image of green grass and the blue sky as a backdrop. Images of a rabbit, a groundskeeper (a man with a lawnmower), a gopher, or a few small birds appear on each screen for 1, 1.5, or 3 seconds at random. The object of the game is to avoid distracters and wait for only an image of a gopher to appear 14, at which time the player should touch the mallet Cube 12 to the gopher Cube 14, which marks a successful hit with a "bonk" noise. Each of the 17 game sessions is 90 seconds long, with a 20-second interval in between each session.

Procedures

All participating subjects were requested to come to one of the test sites for an initial evaluation. They were also asked to play the game "Groundskeeper." Parents of all subjects, including the comparison population, were requested to complete a Conners' Brief Rating Scale, Parent Version. A Teacher Version was supplied to the parent to be completed by a schoolteacher and returned in a pre-addressed envelope. Previous scores from the Conners' CPT were requested from parents if it was previously done for participating subjects. Both the Conners' Brief Rating Scale and the Conners' CPT are highly validated tools commonly used as a research and clinical tool to assess child behavior. The game data were automatically uploaded to a cloud server, and the de-identified data were submitted to the University of Minnesota for analysis.

Figure 2:
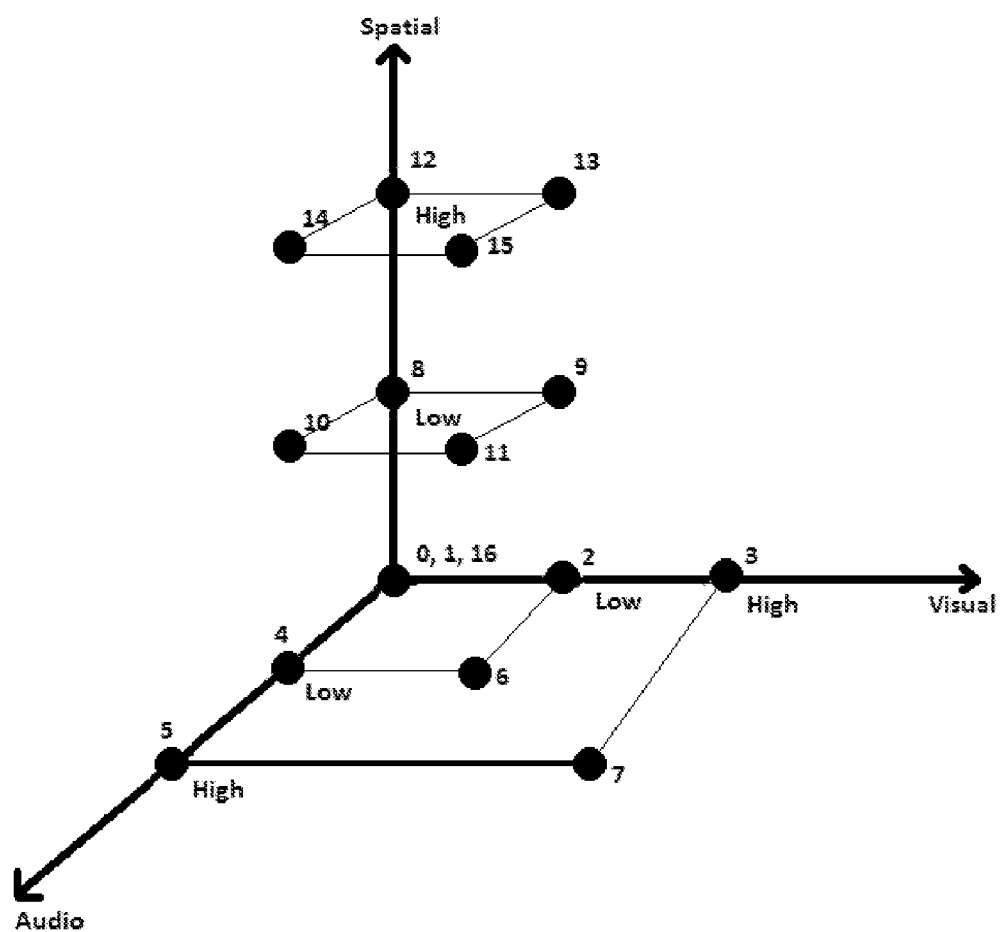
FIG. 2 is a three-dimensional graph illustrating the feature variables measured by different sessions.

FIG. 2 and Table 1.5 shows the design of the overall evaluation protocol, which consists of 17 game sessions, numbered 0 through 16, each with different levels and types of distractions: visual, audio, and spatial, represented by the three coordinate axes. Low visual distraction consists of a bird appearing on the cube screens; high visual distraction adds large rabbits. Low audio distraction consists of occasional tweeting noises; high audio distraction increases tweet frequency. When there is no spatial distraction, the image cubes are in a vertical line. In low spatial distraction, they are set diagonally 2 inches apart as shown in FIG. 1; high spatial distraction consists of each cube put 3 inches apart. Sessions 0, 1, and 16 have no distraction. Each session is 90 seconds long, consisting of randomized number of trials and frequency of target stimulus presentation. Session 0 for practice and is not used for analysis. Session 1 is used to measure the subject's initial ability and focus level, and Session 16 is a control at the end of gameplay in order to measure learning and endurance

TABLE 1.5

Game Levels

Session 0: Screen shot of gopher, groundskeeper or grass (neutral) presented for 1, 1.5 or 3 seconds at a random frequency. This is for instructional purposes only for the patient. This should not be used for analysis.
Session 1: Screen shot of gopher, groundskeeper or grass (neutral) presented for 1, 1.5 or 3 seconds at a random frequency. Go/no go task
Session 2: Gopher, groundskeeper or grass screenshot with visual disturbance at a low degree (one bird showing up on screen) alternating with screenshot of grass presented for 1, 1.5 or 3 seconds at random

TABLE 1.5-continued

Game Levels frequency.
Visual disturbance, low frequency
Session 3: Gopher, groundskeeper or grass screenshot with visual disturbance at a high degree (bird and rabbit) alternating with screenshot of grass presented for 1, 1.5 or 3 seconds at random frequency.
Visual disturbance, high frequency
Session 4: Screen shot of gopher, groundskeeper or grass screenshot presented for 1, 1.5 or 3 seconds at a random frequency with auditory disturbance at a low degree (one bird chirping) occurring at random frequencies for 1, 1.5 or 3 seconds, not in concert with screen shot frequency.
Auditory disturbance, low frequency
Session 5: Screen shot of gopher, groundskeeper or grass screenshot presented for 1, 1.5 or 3 seconds at a random frequency with auditory disturbance at a high degree (multiple birds chirping) occurring at random frequencies for 1, 1.5 or 3 seconds, not in concert with screen shot frequency.
Auditory disturbance, high frequency
Session 6: Gopher, groundskeeper or grass screenshot with visual and auditory disturbances at a low degree (one bird chirping) occurring at random frequencies for 1, 1.5 or 3 seconds
Visual and auditory disturbance, low frequency
Session 7: Gopher, groundskeeper or grass screenshot with visual and auditory disturbances at a high degree (bird and rabbit and chirping) occurring at random frequencies for 1, 1.5 or 3 seconds.
Visual and auditory disturbance, high frequency
Session 8: Gopher, groundskeeper or grass screenshot with spatial disturbance at a low degree. Cube set diagonally. Spaced at 2 inches apart and occurring at random frequencies for 1, 1.5 or 3 seconds.
Spatial disturbance, low frequency
Session 9: Gopher, groundskeeper or grass screenshot with spatial disturbance at a low degree combined with low frequency visual disturbance. Cube set diagonally. Spaced at 2 inches apart and occurring at random frequencies for 1, 1.5 or 3 seconds.
Spatial disturbance, low frequency, low frequency visual disturbance
Session 10: Gopher, groundskeeper or grass screenshot with spatial disturbance at a low degree combined with low frequency auditory disturbance. Cube set diagonally. Spaced at 2 inches apart and occurring at random frequencies for 1, 1.5 or 3 seconds.
Spatial disturbance, low frequency, low frequency auditory disturbance
Session 11: Gopher, groundskeeper or grass screenshot with spatial disturbance at a low degree combined with low frequency visual and auditory disturbance. Cube set diagonally. Spaced at 2 inches apart and occurring at random frequencies for 1, 1.5 or 3 seconds.
Spatial disturbance, low frequency, low frequency visual and auditory disturbance
Session 12: Gopher, groundskeeper or grass screenshot with spatial disturbance at a low degree. Cube set diagonally. Spaced at 3 inches apart and occurring at random frequencies for 1, 1.5 or 3 seconds.
Spatial disturbance, high frequency
Session 13: Gopher, groundskeeper or grass screenshot with spatial disturbance at a high degree combined with low frequency visual disturbance. Cube set diagonally. Spaced at 3 inches apart and occurring at random frequencies for 1, 1.5 or 3 seconds.

TABLE 1.5-continued

Game Levels

Spatial disturbance, high frequency, low frequency visual disturbance
Session 14: Gopher, groundskeeper or grass screenshot with spatial disturbance at a high degree combined with low frequency auditor disturbance. Cube set diagonally. Spaced at 3 inches apart and occurring at random frequencies for 1, 1.5 or 3 seconds.
Spatial disturbance, high frequency, low frequency auditory disturbance
Session 15: Gopher, groundskeeper or grass screenshot with spatial disturbance at a high degree combined with low frequency visual and auditory disturbance. Cube set diagonally. Spaced at 3 inches apart and occurring at random frequencies for 1, 1.5 or 3 seconds.
Spatial disturbance, high frequency, low frequency visual and auditory disturbance
Session 16: Screen shot of gopher, groundskeeper or grass (neutral) presented for 1, 1.5 or 3 seconds at a random frequency.
Go/no go task with learning curve.

In order to isolate different stages of learning, several data aggregations were for specific sessions rather than the overall. Sessions 2 through 7 measured initial learning while including less distraction. Sessions 8 through 11 defined the variable to be considering only the low spatial distraction sections, as well as the late-intermediate portion of their learning. The final stage of the learning curve included sessions 12 through 15, when the most distraction (audio, visual, and high spatial) were being employed and subjects had the most experience with the game. By restricting summations to specific portions of the game, a subject's progression in learning as well as distraction and boredom was taken into account. The difference between various types of distraction was also stressed through these sectioned aggregations in the same way that the accuracy ratio variables compared values from different sections.

The creation of feature variables involved a great deal of trial and error. Initially, design of variables compared across the entire game. As the goals became more refined, new sets of variables were created that were specific for each section. Ultimately, the variables for session-specific tasks were chosen. While creating the comparative rates, percentage values were found to be the most accurate and efficient for the algorithms that were being utilized. These rates were most useful for accuracy measures, especially when comparing different types of distraction by creating ratios out of various session accuracies. For other measurements, total values were used rather than rates. This system was more accurate for behavior such as tilt or response time as the goal was to determine how the patient responded to the environment in general instead of comparing measurements. Table 2 is a table of the variables chosen.

TABLE 2

Data Space

| ID | Variable | Description | Formula and/or Origin |
|---|---|---|---|
| 1 | AccountId | Unique owner/account id mapping to the device registration. | Atomic data from devices. |
| 2 | PlayerId | Unique player id mapping to the player of the game. | Atomic data from device. |
| 3 | GameId | Random id to differentiate game played. | Atomic data from device. |
| 4 | Event | Type of activity occurring in game (hit, tilt, stimulus, distracter, etc.). Configurable. | Game logic. |

TABLE 2-continued

Data Space

| ID | Variable | Description | Formula and/or Origin |
|----|----------|-------------|----------------------|
| 5 | DeviceId | Identifier of device exhibiting event | Atomic data from device. |
| 6 | ImageId | Identifier for image displayed. Configurable. | Gamle logic. |
| 7 | NewImageId | Boolean 1 or 0 variable indicating a new image is displayed or not. NewImageId = 1 when new image is displayed. Decision to display new image can be random or explicit in the game. Configurable. | Game logic. |
| 8 | SessionLevel | Indicator for level in game. Session = Level. Configurable. | Game logic. |
| 9 | TiltFlip | Boolean 1 ot 0. $TiltFlip_1$ when device is flipped over, else flipped back $TiltFlip_0$. | Atomic data from device accelerometer. |
| 10 | TiltX | Total movement of device in X direction. | TiltX = TiltLeft + TiltRight<br><br>Player decision involving game logic. |
| 11 | TiltY | Total movement of device in Y direction. Atomic data from device accelerometer. | TiltY = TiltUp + TiltDown<br><br>Player decision involving game logic. |
| 12 | TiltZ | Total movement of device in Z direction. Atomic data from device accelerometer. | $\sum_{m<TiltZ<n} f(TiltZ)$<br><br>m = $TiltFlip_0$, n = $TiltFlip_1$<br>Player decision involving game logic. |
| 13 | Movement | Total movement in all directions. Aggregate of atomic data from device accelerometer. | Movement = TiltX + TiltY + TiltZ<br><br>Player decision involving game logic. |
| 14 | NeighborEvent | Boolean 1 ot 0 variable indicating cubes moved together from neighboring event. $NeighborEvent_1$ or ON when cubes neighbored, else OFF and $NeighborEvent_0$. | Player decision involving game logic. |
| 15 | TiltLeft | Tile or device left. | TiltLeft ∈ TiltX<br>Atomic data from device accelerometer. |
| 16 | TiltRight | Tilt of device right. | TiltRight ∈ TiltX<br>Atomic data from device accelerometer. |
| 17 | TiltUp | Tilt of device upwards. | TiltUp ∈ TiltY<br>Atomic data from device accelerometer. |
| 18 | TiltDown | Tilt of device downwards. | TiltDown ∈ TiltY<br>Atomic data from device accelerometer. |
| 19 | TiltMiddle | Tilt device return to middle. | Atomic data from device accelerometer. |
| 20 | VirtualTicks | Measurable time unit recorded as ticks which operate within the state machine. Configurable measure. | Game logic. |
| 21 | Correct | Number of correct responses, as deemed by rules in the game, based on responses by a player. For example, game defines correct response as $NeighborEvent_1$ while only | Player decision involving game logic. |

TABLE 2-continued

Data Space

| ID | Variable | Description | Formula and/or Origin |
|---|---|---|---|
| | | defined correct image is displayed. | |
| 22 | Incorrect | Number of incorrect responses game, as deemed by rules in the game, based on responses by a player in a game. For example, game defines incorrect response as $NeighborEvent_1$ while defined correct image is NOT displayed. Incorrect = Commissions. | Player decision involving game logic. |
| 23 | Response | Indicator of player decision | Response = $NeighborEvent_1$ + $NeighborEvent_0$ |
| 24 | ImageDraws | Number of images displayed during the game. Configurable. | Game logic. |
| 25 | CorrectDisplay | Number of correct images displayed during the game, as deemed correct by rules within the game. Configurable. | Game logic. |
| 26 | ImageDisplayLength | Measurement of time image is displayed as defined by the number of VirtualTicks an image is assigned display on device. Configurable. | Game logic. |
| 27 | BirdRabbitDisLength | Display length of special distracter like bird or rabbit. Configurable. | Game logic. |
| 28 | DateTime | Actual date and time stamp of game played. | Atomic data from device time. |
| 29 | DoubleHit | Count for double or multiple neighboring responses of device after primary until next image displayed. | $\sum_{i=m}^{n} x_i$<br><br>m = $Response_2$,<br>n = NewImageId<br>Player decision involving game logic. |
| 30 | FrameElapse | Actual state machine time in ticks elapsed for level and/or game. | Atomic data from device internal clock. |
| 31 | TimeMovement | Amount of movement over virtual time period | Movement/VirtualTicks<br><br>Player decision involving game logic. |
| 31 | BirdCounter | Number of bird distractions displayed. Configurable. | Game logic. |
| 32 | RabbitCounter | Number of rabbit distractions displayed. Configurable. | Game logic. |
| 33 | BirdSoundCounter | Number of special sound distractions played. Configurable. | Game logic. |
| 34 | TopBottomHit | Measured by response to top or bottom of device. Count for device responses or hits from top or bottom. | Player decision involving game logic. |
| 35 | CubedPressed | Number of physical touches or presses to device surface. | Atomic data from device accelerometer. |
| 37 | ResponseCounter | Measurement of time between image displays, acts as control for response correct/incorrect. | $\sum_{m<VirtualTicks<n} f(VirtualTicks)$<br><br>m = $Response_x$<br>n = NewImageId<br>Player decision involving game logic. |

TABLE 2-continued

Data Space

| ID | Variable | Description | Formula and/or Origin |
|---|---|---|---|
| 38 | CubeLocation | Geomteric coordinates of the device physical location based on atomic game data. | Player decision involving game logic. |
| 39 | DeviceDistance | Fixed distance in inches devices may be played apart. This varies by type of game and will vary by session as part of setup. | Game logic. |

Correct responses and incorrect responses are recorded for accuracy measures. Omissions (lack of response to a gopher image) and commissions (responding to an incorrect image) are also counted. Other behavioral responses are also observed, such as DoubleHit, or hitting the cube twice quickly. This specific type of commission error tends to arise when a person thinks they have not adequately hit the gopher and is an indication of hyperactivity. ResponseCounter measures how long two cubes are pressed together, from the time of contact to the time of release. This aids in detecting inattentiveness and hyperactivity even in a combined patient whose overall timing may be similar to that of a normal subject. Patients with a diagnosis of ADHD-combined type tend to start slow, but hit the cubes together very quickly. Finally, ResponseCorrect and ResponseIncorrect measure the time from which an image is displayed until a response is hit, with correct and incorrect responses noted respectively.

Measures of distractibility included mCRR (motor correct response rate) and mIRR (motor incorrect response rate). These measure the number of correct or incorrect responses by the total responses respectively. Further accuracy measures included mEOM (omissions divided by correct responses—an indicator of inattention). These divide the mIRR to clarify if patients have excessive motion and stimulation as opposed to lethargy and lack of stimulation. Omissions and commissions were also placed as raw numbers to provide a more direct comparison between trial identifiers. DoubleHit was calculated as a raw number of the times a person hurriedly struck the gopher twice, an indicator of impulsivity and scattered, fast behavior.

Further assessment was then conducted on performance between sessions. Comparisons between visual and audio distractors and subsequent accuracy allowed evaluation of mCRRs and mIRRs at different intensities of distraction. A higher level of failure appeared to indicate that external distractors had a more profound impact on the subject. Comparison of the success and failure rates for different combinations of distractors and intensities allowed investigators to determine if audio or visual distractors were more problematic for the subject. This was determined by comparing the mCRR of a session containing only one type of distraction to a session with both. The intensity of distraction remained constant in each comparison, resulting in the variables instead of two. Spatial accuracy was then compared between sessions containing short distances between the cubes against those with increased distance. While other factors remained constant, the mCRRs of the spatial distractor sessions were assessed. For example, Session 6 (low audio, low visual) was compared to Session 11 (low audio, low visual, low spatial) by making a ratio of their comparative mCRRs. Spatial success/failure ratio was created to compare varying degrees of spatial distraction, comparing the mCRR of low distraction (Session 8) to that of high distraction (Session 12). The complete spatial success/failure ratio utilized the same approach, but involved audio and visual distractors as constant factors.

Finally, LearningCurve was used to measure learning. The percentage of improvement was calculated between Session 16 and Session 1 to determine if the subject had improved, thus learning, or had gotten worse, implying boredom or distraction.

In-game behavior features were more extensively investigated. TiltX, TiltY, and TiltZ were aggregations of degrees of tilt throughout each session. The greater the degree of tilt, the more indicative of hyperactive behavior, especially in the case of TiltZ which is the most extreme motion. OffTiltReaction and OnTiltReaction were summed to specify how much the person moved the cube around before and after making a response. More movement implied more distraction surrounding a response, whereas less movement could indicate either more focus or simply less activity. CorrectReaction and IncorrectReaction were summed to determine slower versus quicker speeds—less speed implying inattention. As these two measures would be abnormally slow for inattentive patients while remaining comparatively equal for ADHD-combined type and non-ADHD patients, NeighborReaction was summed to isolate the amount of time that two cubes were pressed together. As stated previously, an ADHD-combined type patient would start slowly and, once they got closer, press the cubes together and let go quickly, becoming more engaged and impulsive as the stimulation set in. However, a non-ADHD subject would be more balanced in their time distribution. Thus, NeighborReaction differentiates reaction time between ADHD-combined type and non-ADHD subjects.

Some variables were used as extraneous distraction collectors—movements that should not take place during gameplay that could signify hyperactive behavior. These included TopBottomHit, a sum of all hits to the tops or bottoms of cubes, and CubePressed, a count of how many times the screen was pressed in.

In order to isolate different stages of learning, several data aggregations were for specific sessions rather than the overall. Sessions 2 through 7 measured initial learning while including less distraction. Sessions 8 through 11 defined the variable to be considering only the low spatial distraction sections, as well as the late-intermediate portion of their learning. The final stage of the learning curve included sessions 12 through 15, when the most distraction (audio, visual, and high spatial) were being employed and subjects had the most experience with the game. By restricting summations to specific portions of the game, a subject's progression in learning as well as distraction and boredom was taken into account. The difference between various types of distraction was also stressed through these sectioned aggregations in the same way that the accuracy ratio variables compared values from different sections.

Data Analysis Procedures

The game collects data samples of 33 variables (Table 2, IDs 4-37) at 10 Hz. Over 17 sessions of 90 seconds each, this translates to 15,300 samples per participant. This is a rich and granular dataset of gameplay behavior, from which detailed diagnostic models can be built. In the experiment, data from 52 participants were used to build predictive models for hyperactivity, inattentiveness, and control.

Machine Learning-Based Approach to ADHD Diagnosis

The data from the game were mathematically transformed into feature variables corresponding to specific neurological correlates designated by the child/adolescent psychiatrists. After feature creation, a principal component analysis was applied to generate the most useful features. The transformed data were analyzed using Waikato Environment for Knowledge Analysis, a suite of open sthece machine learning software.

Figure 3:
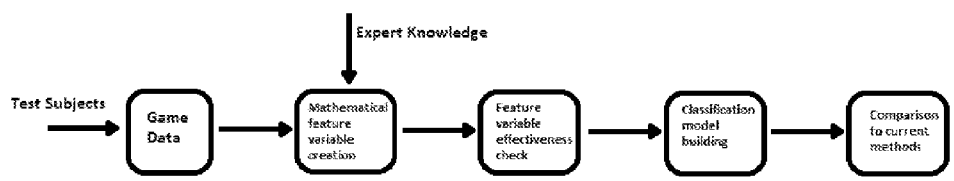
FIG. 3 is a flow diagram illustrating the machine learning feedback algorithm.

Once a highly accurate algorithm with successful feature variables was created, the parameters became the diagnostic tool (FIG. 3).

Feature Space for ADHD Diagnosis

Success of data-driven model building is highly dependent on the feature space used for the analysis, which can differ from the variables collected. Using domain knowledge to transform the data variables collected into a feature space suitable for effective model building is one of the key innovations of this study. Along with traditional game elements and events acting as identifiers within the game, each data instance contained several data variables. There are various tilt variables that measure different aspects of movement, game-environment variables that count images, time measurements of responses and actions, extraneous action variables that measure cube pressing, hits that shouldn't occur, and accuracy variables.

It was found that totals and rates were useful for feature variable creation. Because each session is different in order to avoid predictability, rates were used to normalize subject results. Aggregations of in-game data were also used to highlight differences that would be missed in sequential data. Accuracy measures were made to identify patterns that would be distinctive of the three possible cases. It was predicted that normal subjects have the highest accuracy, inattentive patients have the highest omission rate (lack of a response to stimuli), and combined patients have the highest commission rate (incorrect/extraneous hits). Comparisons between different sessions were included in order to measure effects of different types/intensities of distraction on accuracy. Learning was measured for both diagnosis and potential treatment purposes through a variable called LearningCurve, calculated by the percentage improvement between Session 16 and Session 1, illustrating improvement and thus learning, or regression, implying boredom or distraction.

In-game behavior features included aggregations of degrees of tilt throughout each session; high tilt is representative of hyperactive behavior. Reaction timings were summed to differentiate between speeds, with slower implying inattention. Additional measures were included to differentiate among ADHD, combined type, and normal subjects who demonstrated similar reaction times but varying patterns of behavior when reacting to visual stimuli. Some variables were extraneous distraction collectors—movements that were uncommon could imply hyperactive behavior. Several of the aggregations were through specific sets of sessions rather than the overall game in order to isolate different stages of a person's learning as he or she progressed in the game, from which intermediate models were created. Principal component analysis was then applied to reduce dimensionality and to determine the most distinctive feature variables for the model.

The classification algorithms were tested during model creation: AdaBoost, JRip, J48, and RandomForest. AdaBoost is a meta-algorithm, meaning that it creates solutions and progressively improves them, JRip is a rule-making algorithm, and J48 and RandomForest are decision trees that create parameters and split the data based on them.

The below Table 2.5 summarizes the feature space mathematical transformations:

TABLE 2.5

Feature Space, mathematical transformations of data space

| ID | Variable | Description | Formula |
|----|----------|-------------|---------|
| 1 | OffTiltReaction | Off response tilt counter. Counter increments on each tilt from point of device neighbor removal (after neighboring) until next image displayed | $\sum_{m<TimeMovement<n} f(TimeMovement)$<br>$m = Response_x$<br>$n = NewImageId$ |
| 2 | OnTiltReaction | On response tilt counter. Counter increments on each tilt from point new image is displayed until devices are neighbored | $\sum_{m<TimeMovement<n} f(TimeMovement)$<br>$m = Response_x$<br>$n = NewImageId$ |
| 3 | ResponseCorrect | Measurement of time when an image is displayed until correct response is regeistered. Delta between response counter measures response time. | $\sum_{m<VirtualTicks<n} f(VirtualTicks)$<br>$m = Response_x$<br>$n = NewImageId$ |

TABLE 2.5-continued

Feature Space, mathematical transformations of data space

| ID | Variable | Description | Formula |
|---|---|---|---|
| 4 | ResponseIncorrect | Measurement of time when image is displayed until incorrect response is regeistered. Delta between response counter measures response time. | $\sum_{m<VirtualTicks<n} f(VirtualTicks)$<br>$m = Response_{correct}$<br>$n = NewImageId$ |
| 5 | NeighborReaction | Measurement of time from when two devices are put together (neighbored) until the moment they are removed. | $\sum_{m<VirtualTicks<n} f(VirtualTicks)$<br>$m = NeighborEvent1$<br>$n = NeighborEvent0$ |
| 6 | CorrectReaction | Measurement of time from when an image is displayed until a correct response. | $\sum_{m<VirtualTicks<n} f(VirtualTicks)$<br>$m = Response_{correct}$<br>$n = NewImageId$ |
| 7 | IncorrectReaction | Measurement of time from when an image is displayed until an incorrect response. | $\sum_{m<VirtualTicks<n} f(VirtualTicks)$<br>$m = Response_{incorrect}$<br>$n = NewImageId$ |
| 8 | ErrorOmission | Number of times the correct stimulus is presented and there is no response. | ErrorOmission = CorrectDisplay − Correct |
| 9 | mCRR | Ratio of correct to incorrect and correct | Correct/(Incorrect + Correct) |
| 10 | mIRR | Ratio of incorrect to incorrect and correct | Incorrect/(Incorrect + Correct) |
| 11 | mEOM | Ratio of omissions to incorrect and correct | (ErrorOmission)/(Incorrect + Correct) |
| 12 | mMMO | Mallet movement only (multiple for various levels of game) | $\sum_{i=m}^{n} x_i$<br>$m = mMMO \in Movement$ |
| 13 | mAOM | Sum of all movement excluding mallet cube (multiple for various levels of game) | $\sum_{i=m}^{n} x_i$<br>$m = mAOM \in Movement$ |
| 14 | mCT | Total maximum tilt measurements (multiple for various levels of game) | TiltX + TiltY + TiltZ |
| 15 | LearningCurve | Learning Curve | ((mCRR16/mCRR1) − 1) * 100 |
| 16 | LearningCurve_O | Learning Curve of Omissions | ((((mCRR16/mCRR1)/(mEOM16/mEOM1)) − 1) * 100) |
| 17 | LearningCurve_NR | Learning Curve Neighbor Reaction | (((mNR16/mNR1) − 1) * 100) |
| 18 | LearningCurve_CR | Learning Curve of Correct Reaction | (((mCR16/mCR1) − 1) * 100) |
| 19 | LearningCurve_CT | Learning Curve of Cuber Tilts | (((mCT16/mCT1) − 1) * 100) |
| 20 | LearningCurve_ICR | Learning Curve of Incorrect Responses | (((mICR16/mICR1) − 1) * 100) |
| 21 | VSC_VFC | Visual Success Comparison | (mCRR2/mCRR3)/(mIRR2/mIRR3) |
| 22 | VSC_VFC_O | Visual Omission Comparison | (mCRR2/mCRR3)/(mEOM2/mEOM3) |
| 23 | ASC_AFC | Auditory Success Comparison | ((mCRR4/mCRR5)/(mIRR4/mIRR5)) |
| 24 | ASC_AFC_O | Auditory Omissions Comparison | ((mCRR4/mCRR5)/(mEOM4/mEOM3)) |
| 25 | CSSC | Spatial Success Comparison | mCRR11/mCRR15 |
| 26 | CSSC_O | Spatial Omissions Comparison | mEOM11/mEOM15 |

TABLE 2.5-continued

Feature Space, mathematical transformations of data space

| ID | Variable | Description | Formula |
|---|---|---|---|
| 27 | CSSC_IRR | Complete Spatial Failure Comparison | mIRR11/mIRR15 |
| 28 | SCC_SFC | Spatial Success against Incorrect to Low Spatial and Visual and Auditory Comparison | ((mCRR6/mCRR11)/(mIRR6/mIRR11)) |
| 29 | SSC_SFC_O | Spatial Success against Omissions to Low Spatial and Visual and Auditory Comparison | (mCRR6/mCRR11)/(mEOM6/mEOM11) |
| 30 | SSC_SFC_NR | Spatial Neighbor Reaction Comparison Low Frequency | (mNR6/mNR11) |
| 31 | SSC_SFC_CR | Spatial Correction Reaction Comparison Low Frequency | (mCR6/mCR11) |
| 32 | SSC_SFC_IR | Spatial Incorrect Comparison Low Frequency | (mICR6/mICR11) |
| 33 | CVSC_CVFC | Visual Success against Incorrect of Visual Low to Visual and Auditory Low Compared to Visual High and Visual and Auditory High Compared with Spatial Effects of the Same Distractors | (((mCRR2/mCRR6)/(mCRR3/mCRR7))/((mIRR2/mIRR6)/(mIRR3/mIRR7))) |
| 34 | CVSC_CVFC_O | Visual Success against Omissions of Visual Low to Visual and Auditory Low Compared to Visual High and Visual and Auditory High Compared with Spatial Effects of the Same Distractors | ((mCRR2/mCRR6)/(mCRR3/mCRR7)).((mEOM2/mEOM6)/(mEOM3/mEOM7)) |
| 35 | CASC_CAFC | Auditory Success against Incorrect of Auditory Low to Visual and Auditory Low Compared to Auditory High and Visual and Auditory High Compared with Spatial Effects of the Same Distractors | ((mCRR4/mCRR6)/(mCRR5/mCRR7))/((mIRR4/mIRR6)/(mIRR5/mIRR7)) |
| 36 | CASC_CAFC_O | Auditory Success against Omissions of Auditory Low to Visual and Auditory Low Compared to Auditory High and Visual and Auditory High Compared with Spatial Effects of the Same Distractors | ((mCRR4/mCRR6)/(mCRR5/mCRR7))/((mEOM4/mEOM6)/(mEOM5/mEOM7)) |

Results

Model Evaluation

Two types of evaluations of the model have been performed, details of which are described in this section. The first, proposed by Fisher, 23 uses a significance level to assess if the data collected from "Groundskeeper" play have sufficient information to be used for building a diagnosis model, a hypothesis. The second approach, the Neyman-Pearson approach, 23 was used to compare the performance of the proposed diagnosis model against that of existing models by Type I and Type II error calculations. In the following section the models are described evaluations in detail.

P Value-Based Analysis

Table 3 shows the results of the P value analysis for inattention and combined deficits of the 52 subjects. The expected values were the diagnoses provided by expert psychiatric evaluation using a semistructured interview. The observed values were the calculated diagnoses produced by the model. For comparison, P values for the CPT ranged from <0.0001 to 0.88, depending on the variable analyzed.

TABLE 3

P VALUE SCORES FOR INATTENTION AND COMBINED DEFICITS

| | Yes | No | Total |
|---|---|---|---|
| Inattention[a] | | | |
| Observed | 20 | 32 | 52 |
| Expected | 26 | 26 | 52 |
| | 5.95 | 5.95 | |
| | 35.4025 | 35.4025 | |
| $\chi^2$ statistic | 1.361635 | 1.361635 | 2.723269 |

TABLE 3-continued

P VALUE SCORES FOR INATTENTION
AND COMBINED DEFICITS

|  | Yes | No | Total |
|---|---|---|---|
| Combined[b] | | | |
| Observed | 10 | 42 | 52 |
| Expected | 17 | 35 | 52 |
|  | 6.95 | 6.95 | |
|  | 48.3025 | 48.3025 | |
| $\chi^2$ statistic | 2.841324 | 1.380071 | 4.221395 |

[a]One degree of freedom, two-tailed P = 0.0989.
[b]One degree of freedom, two-tailed P = 0.0399.

Figure 4:
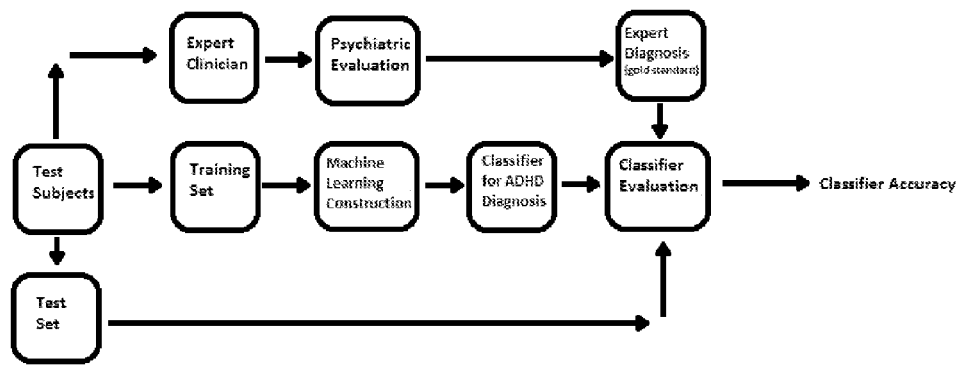
FIG. 4 is a flow diagram illustrating a method of evaluating quality of the game platform method in variables chosen.

Effect size and accuracy of measurement vary by variable measured based on CPT testing (for example, commissions, omissions, reaction time, standard deviation of reaction time, etc.). For the Conners' test, internal consistency coefficients for the total sample ranged from 0.77 to 0.97 (all correlations significant, P<0.001). Inter-rater reliability coefficients ranged from 0.52 to 0.94. The P value scores obtained for the approach, in its early stage, is extremely promising. The results will improve as the approach is tested and fine-tuned over larger-scale studies. Type I and Type II error-based analysis In order to maximize accuracy, the model was split into two binary classifications: Presence/absence of hyperactivity and presence/absence of inattention. The hyperactive and inattentive components of ADHD, combined type, had a Yes indication for each in the dataset. An ADHD, inattentive type patient would have a Yes for inattention and a No for hyperactivity, and a normal/control patient would have No for both. Thus, the algorithms were able to take advantage of variables specific to one type of ADHD instead of dealing with results from the different classes of the disorder. The combined model, utilizing the F-measure (harmonic mean between precision and recall), ultimately classified the subjects with 75 percent accuracy. The inattention model had 78 percent accuracy. Frequently combined with ADHD, anxiety, depression, and autism spectrum disorders (ASD) also have deficits of executive functioning. With certain specifications of variables, the models had 71 percent accuracy for anxiety and 76 percent for depression. There was not a large enough sample to determine the model accuracy for diagnosing ASD (FIG. 4 and Table 4).

TABLE 4

DIAGNOSIS MODEL RESULTS

|  | Predicted no | Predicted yes |
|---|---|---|
| Model Inattention (n = 52, treatment and control population)[a] | | |
| Actual no | 21 | 5 |
| Actual yes | 6 | 20 |
| Model Combined (n = 52, treatment and control population)[b] | | |
| Actual no | 29 | 6 |
| Actual yes | 7 | 10 |
| CPT Inattention (n = 21, treatment and control population)[c] | | |
| Actual no | 16 | 1 |
| Actual yes | 1 | 3 |
| CPT Combined (n = 33, treatment and control population)[d] | | |
| Actual no | 19 | 2 |
| Actual yes | 1 | 11 |

TABLE 4-continued

DIAGNOSIS MODEL RESULTS

|  | Predicted no | Predicted yes |
|---|---|---|
| Conners' Inattention Parent (n = 9 for treatment, n = 24 for control)[e] | | |
| Actual no | 14 | 10 |
| Actual yes | 3 | 6 |
| Teacher (n = 23 for treatment, n = 24 for control)[f] | | |
| Actual no | 20 | 4 |
| Actual yes | 11 | 12 |
| Conners' Combined Parent (n = 17 for treatment, n = 24 for control)[g] | | |
| Actual no | 14 | 10 |
| Actual yes | 3 | 14 |
| Teacher (n = 15 for treatment, n = 24 for control)[h] | | |
| Actual no | 20 | 4 |
| Actual yes | 7 | 8 |

[a]False-positive = 5, true-positive = 20, false-negative = 6, true-negative = 21; sensitivity = 0.769, specificity = 0.807.
[b]False-positive = 6, true-positive = 10, false-negative = 7, true-negative = 29; sensitivity = 0.588, specificity = 0.828.
[c]False-positive = 1, true-positive = 3, false-negative = 1, true-negative = 16; sensitivity = 0.75, specificity = 0.941.
[d]False-positive = 2, true-positive = 11, false-negative = 1, true-negative = 19; sensitivity = 0.916, specificity = 0.904.
[e]False-positive = 10, true-positive = 6, false-negative = 3, true-negative = 14; sensitivity = 0.666, specificity = 0.833.
[f]False-positive = 4, true-positive = 12, false-negative = 11, true-negative = 20; sensitivity = 0.916, specificity = 0.904.
[g]False-positive = 10, true-positive = 14, false-negative = 3, true-negative = 14; sensitivity = 0.823, specificity = 0.583.
[h]False-positive = 4, true-positive = 8, false-negative = 7, true-negative = 20; sensitivity = 0.533, specificity = 0.833.
CPT, Continuous Performance Test.

Comparison of the Proposed Approach with Existing Methods

Figure 5:
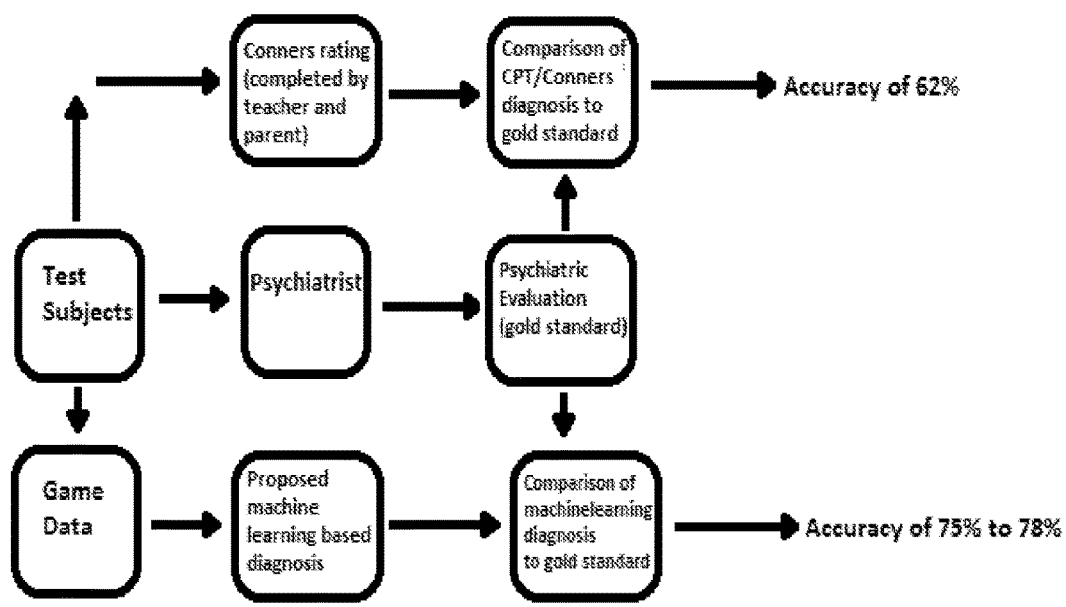
FIG. 5 is a flow diagram comparing the accuracy of the game platform method versus a pre-existing method.

After the models were generated, the accuracy/F-measure for each model was evaluated against the psychiatrist's diagnosis. The results from subjects' parents/teachers Conners' Brief Rating Scales and the subjects' CPT score were used to provide clinical support for the diagnosis. The results for ADHD determination were divided into inattention and hyperactivity models. Additionally, a confusion matrix was constructed to convey these symptoms for all three methods, which is shown in Table 3. The complexity added by the Conners' Brief Rating Scale resulted in dividing this specific matrix by the Parent and Teacher Versions (FIG. 5). Inattentive type. In the study, subjects with ADHD, inattentive type, were accurately diagnosed by the CPT 75 percent of the time. Conners' Brief Rating Scale, Parent Version represented an inattention subscale average tilt (T) score of 81.66 (a T score of >70.0 is clinically significant) by which six out of nine subjects were correctly diagnosed, or 67 percent accuracy. The Conners' Brief Rating Scale, Teacher Version represented an inattention subscale average T score of 62.37, by which two out of eight subjects were correctly diagnosed, or 25 percent accuracy. The predictive model provided accuracy of 78 percent. Combined type. For subjects with ADHD, combined type, the CPT had accuracy of 91.66 percent. Conners' Brief Rating Scale, Parent Version represented an inattention subscale average T score of 80.71 and a hyperactivity subscale average T score of 82.12. Fifteen out of 17 correctly identified subjects with ADHD, combined type, or 82 percent. The Conners' Brief Rating Scale, Teacher Version represented an inattention subscale average T score of 74.87 and a hyperactivity subscale average T score of 76.07. Eight out of 15 subjects were correctly identified as ADHD, combined type, or 53 percent accuracy. The predictive model provided accuracy of 75 percent. Controls. For control subjects, the CPT was 94.11 percent accurate. Conners' Brief Rating Scale, Parent Version represented an inattention subscale average T score of 64.79 and a hyperactivity subscale average T score of 60.21. Fifteen out of 24 subjects were correctly identified as not having ADHD, or 58 percent accuracy. For the Teachers Version, the inattention subscale average T score was 59.83, and the hyperactivity subscale average was 57.91. Twenty out of 24 subjects were correctly identified as not having ADHD, or 83 percent accuracy. The predictive model provided accuracy of 80.77 percent for inattention controls and 82.86 percent for combined type controls.

Discussion

This study shows "Groundskeeper" has the potential to improve accuracy and access to diagnostics of disorders with executive functioning deficits through objective data collection methods using multisensor technology. The main study findings were that the game played on the Sifteo Cubes was able to accurately detect ADHD, combined type, 75 percent of the time and ADHD, inattentive type, 78 percent through machine learning techniques. The game was also able to accurately detect anxiety 71 percent of the time and depression 76 percent of the time. No conclusions were made regarding the assessment of ASD through gameplay given the limited number of participants. These results suggest this game is successful in identifying executive functioning deficits and differentiating based on patterns of behavior among ADHD, combined type, ADHD, inattentive type, anxiety, and depression with high accuracy. In the study, the results were with the participants' performance on the CPT and by the Conners' Brief Rating Scale, Parent and Teacher Versions. These tests in the study population, who were recruited from a higher level of care, were more predictive than "Groundskeeper." However, the clinical severity of the participant's mental health diagnoses was above average, indicated by not only the severity but also the frequency of comorbidities, which may have contributed to the increased accuracy of these measures in comparison with previously quoted reliability scores by Conners and other studies using these tools. Games provide a fun and engaging way of gathering data through play that can identify aberrant patterns of behavior indicative of ADHD and other mental health diagnoses. Additionally, through the use of the Sifteo Cubes, not not only can response data be collected, but also behavior exhibited by the participant in between responses. By capturing a vast array of behavioral data, small components of volitional and involuntary movement may be analyzed that may provide additional clues for diagnostics of cognitive disorders. Although the CPT and the Conners' Brief Rating Scale were found to be more accurate compared with the method, several considerations suggest that further pursuit of the approach is warranted. First, the approach was successful. It has several advantages over other clinical diagnostic aids. There are practical logistical advantages using the approach. Based on the results presented in Table 4, it is evident that obtaining CPT scores from every subject was a challenge. Only 33 subjects exhibited symptoms that warranted this expensive computer-based test. Also, for the Conners' Brief Rating Scales, six subjects did not return one or all of the forms. This suggests a significant effort in coordination and time to complete testing. "Groundskeeper" is as accessible as the Conners' Rating Scales but does not require this coordination. Furthermore, given its vast quantity of multidimensional data, the approach may prove to have a better ability to assess simultaneously symptoms across interrelated psychiatric disorders that show high comorbidity. This may help to provide important insight into convergent and divergent aspects of related forms of psychopathology. Given the accessibility of the game medium and ease of use, the machine learning-based diagnostic aid method can become widespread and improve diagnosis accuracy for executive functioning disorders. The introduction of more feature variables and/or a more precise algorithm could improve the model accuracy. The algorithm shapes the model to the training set, which may cause extra error during cross-validation or when applying to a new test set. Another potential source of error in the feature variable creation is a small scale that did not magnify differences sufficiently. Feature variable creation, selection, and additional algorithm testing on a larger sample are primary extensions of this project. Additionally, with a large enough population, patterns of responses can be analyzed for those with ASD.

Path variables are properties of the path traversed by the mallet cube, and are a key innovation of this project. Since the cubes can measure movement and interact with each other, position of the cubes can be mapped and analyzed. These variables highlight inattention and hyperactivity and create scales for various manifestations of executive functioning disorders.

Figure 6:
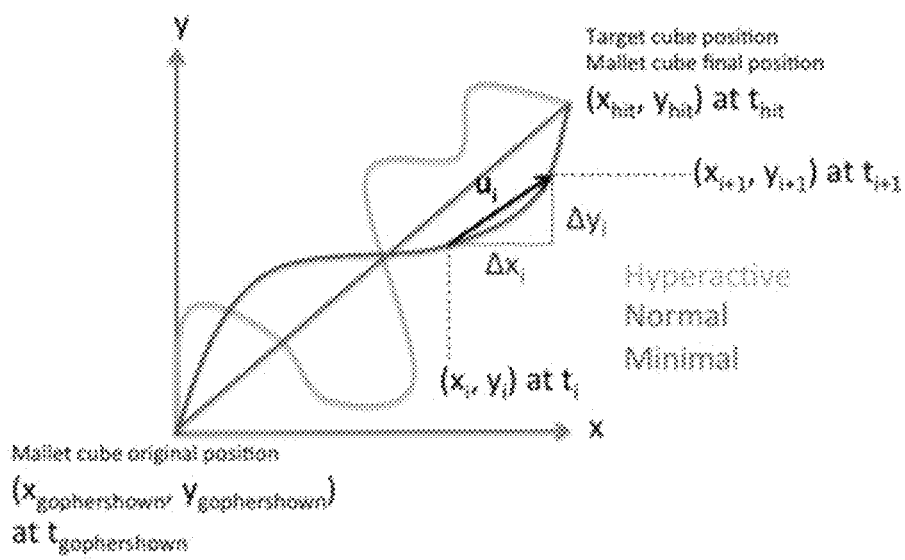
FIG. 6 is a graph of the path traversed by a mallet cube until a hit comparing paths taken by normal and hyperactive patients.

FIG. 6. General pathways for a response are shown—the minimal pathway would be a straight line from origin (mallet cube placement at time of gopher stimulus being shown) to final position (mallet cube placement at time of hit). A normal patient is postulated to have some curvature and extraneous movement, while a hyperactive patient is expected to have a larger amount.

Let $t_{gophershown}$: the tick at which a gopher is shown, with position $(x_{gophershown}, y_{gophershown})$ $t_{hit}$: the tick at which the cube is hit, with position $(x_{hit}, y_{hit})$ As shown in FIG. 6, the displacement vector $u_i$ from $(x_i, y_i)$ at tick $t_i$ to $(x_{i+1}, y_{i+1})$ at tick $t_{i+1}$ can be broken down into x-component $\Delta x_i$ and y-component $\Delta y_i$.

$$\|u_i\| = \sqrt{\Delta x_i^2 + \Delta y_i^2}$$

The sum of magnitudes of all displacement vectors in a response is the best approximation of the length of the path taken in that response. The length of the minimal path shown in blue in FIG. 6, the net displacement from the position of the mallet cube at $t_{gophershown}$ to its position at $t_{hit}$, can be considered the most efficient response path.

$$\text{Path Length Approximation:} \sum_{i=gophershown}^{hit} \|u_i\|$$

$$\text{Net Displacement} = \sqrt{(x_{hit} - x_{gophershown})^2 + (y_{hit} - y_{gophershown})^2}$$

The ratio of these two values is a distance ratio of actual to minimal. It indicates the degree of extraneous movement.

$$\text{Distance Ratio} = \frac{\text{Path Length Approximation}}{\text{Net Displacement}}$$

Note that in the case of an omission, because a $(t_{hit}, x_{hit}, y_{hit})$ would never occur, the final x and y positions in the Path Length Approximation are $x_{gopherremoved}$ and $y_{gopherremoved}$ at $t_{gopherremoved}$, the tick at which the gopher is removed from the target cube screen. The positions are of the mallet cube. For Net Displacement, $x_{hit}$ and $y_{hit}$ are replaced with $x_{gopherremoved}$ and $y_{gopherremoved}$ of the target cube.

Figure 7:
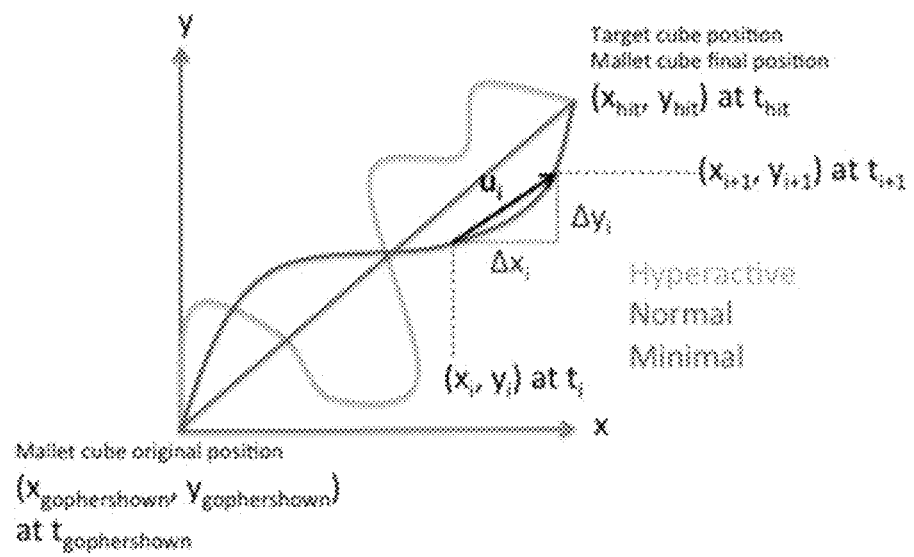
FIG. 7 is a second graph showing a mallet cube path and measure of path change between two successive ticks.

FIG. 7. The vectors shown ticks i to i+1 and i+1 to i+2, two consecutive vectors, have an angle between them that indicates extraneous directional change. A hyperactive patient is postulated to have more directional change than a normal person. The angle in the diagram is given as $\theta_i$.

As shown in FIG. 7, as multiple displacement vectors are found, the angle between them shows a directional change. In order to find the angle, two consecutive displacement vectors are dotted.

$$u_i \cdot u_{i+1} = (\Delta x_i * \Delta x_{i+1}) + (\Delta y_i * \Delta y_{i+1})$$

The dot product is then divided by both magnitudes and the inverse cosine of the result is taken in order to calculate the angle of directional change, shown in FIG. 7 as $\theta_i$.

$$\theta_i = \arccos\left(\frac{(\Delta x_i * \Delta x_{i+1}) + (\Delta y_i * \Delta y_{i+1})}{\sqrt{\Delta x_i^2 + \Delta y_i^2}\sqrt{\Delta x_{i+1}^2 + \Delta y_{i+1}^2}}\right)$$

Once all the angles are found, they are summed to find total directional change. This sum is divided by the total number of directional change records. Each record requires three points, i.e. three ticks, and the sets of three consecutive ticks can overlap. Therefore:

$$\text{Total Directional Change} = \sum_{i=gophershown}^{hit} \theta_i$$

$$\text{Total Angle Records} = t_{hit} - t_{gophershown} - 2.$$

The Total Directional Change divided by the Total Angle Records yields an average directional change for the response.

$$\text{Average Directional Change} = \frac{\text{Total Directional Change}}{\text{Total Angle Records}}$$

Note that in the case of omissions, all the final positions are ($x_{gopherremoved}$, $y_{gopherremoved}$) of the mallet cube and instead of $t_{hit}$, the final tick is $t_{gopherremoved}$.

Figure 8:
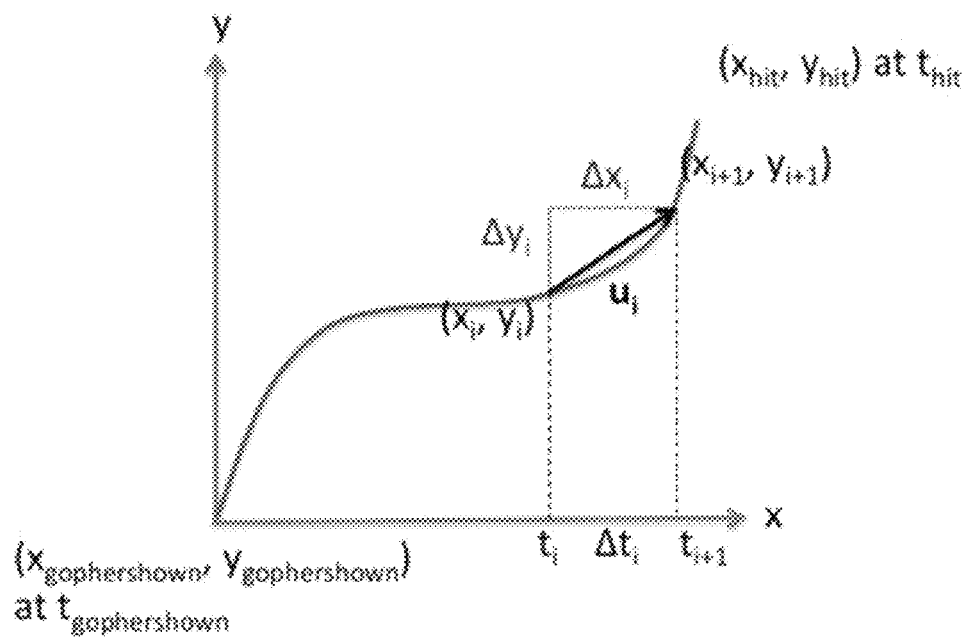
FIG. 8 is a third graph showing a mallet cube path and the velocity of a change in path.

FIG. 8. By dividing a displacement vector by the change in time it occurs over, average velocity can be found. Done for each tick, this displays the range of velocities in a response path. An inattentive patient is expected to have low velocities.

As shown in FIG. 8, the change in time can be obtained and used to find the average speed between two ticks. In this project, the speed was found between each consecutive pair of ticks, so $\Delta t = 1$.

$$\text{Speed}_i = \frac{\sqrt{\Delta x_i^2 + \Delta y_i^2}}{\Delta t}$$

Each record of speed is taken between two points, and consecutive pairs can overlap. Therefore:

$$\text{Total Speed Records} = t_{hit} - t_{gophershown} - 1$$

The average speed for a response can now be calculated as:

$$\text{Average Speed} = \frac{\sum_{i=t_{gophershown}}^{t_{hit}} \frac{\sqrt{\Delta x_i^2 + \Delta y_i^2}}{\Delta t}}{\text{Total Speed Records}}$$

Note that in the case of omissions, $t_{hit}$ is replaced by $t_{gopherremoved}$ and $x_{hit}$ and $y_{hit}$ are replaced by $x_{gopherremoved}$ and $y_{gopherremoved}$ of the mallet cube.

These variables highlight inattention and hyperactivity and create scales for various manifestations of executive functioning disorders. After being created for each showing of the gopher in the game, the average, standard distribution, variance, and interquartile range were calculated for individual sessions, and the average of each of these was calculated for the whole game, creating around half of the feature variables created in our analysis. These were created not only to use the gopher-specific measures, but also because variance in performance, as opposed to consistently abnormal performance, can manifest itself in an EFD patient. For example, variance in the average speed across a child's response to multiple gophers stimuli is a good indicator of hyperactivity and/or inattention. Therefore, the standard deviation, variance, interquartile range, and range indicate EFD, in addition to the mean.

CONCLUSIONS

In brief, the methods provide extremely rich datasets that aid clinical analysis and decision making. Collecting data along multiple dimensions of expressed behavioral deficits, specifically the response to audio, visual, and spatial stimuli, represents a potent novel approach. In particular, the ability to quantitatively identify the distortion of motor and cognitive skills linked to cognitive deficits may help lead to a better quality of care.

We claim:

1. A method of diagnosing Attention Deficit Hyperactivity Disorder (ADHD) employing a system comprising a plurality of cubes, each cube comprising a tangible computer that:
   wirelessly communicates with a game computer;
   includes a display on one side, wherein the display displays an image received from said game computer;
   wherein a cube wirelessly communicates motion information to said game computer, the method comprising:
   employing on said game computer a tangible-graphical interactive game with a patient that requires a patient to move a mallet cube to hit a gopher cube, wherein the mallet cube displays on its display a mallet image; and wherein the gopher cube displays on its display a gopher image;
   the tangible-graphical interactive game using motion information from the mallet cube to determine the movement of the mallet cube in at least 2 dimensions from a starting position until the mallet cube hits the gopher cube to generate measurement metrics; and
   generating from said measurement metrics a signal that indicates whether there is a likelihood that the patient has ADHD.

2. The method of claim 1 wherein the signal is generated from an algorithm that employs variables; wherein the variables comprise selected measurement metrics which are determined iteratively employing a machine learning feedback algorithm.

3. The method of claim 1 wherein the generating step comprises employing a Random Forest algorithm.

4. The method of claim 1, wherein tangible-graphical interactive game determines from said measurement metrics a path that comprises the locations of the mallet cube from a starting position until a final position when the mallet cube hits the gopher cube and wherein a path having excessive movement is indicative of a hyperactive patient.

5. The method of claim 4 wherein a path has excessive movement when a total length of a path exceeds a most efficient path.

6. The method of claim 5 wherein the total length of a path is determined by the sum of its displacement vectors, wherein a displacement vector is determined by successive locations and direction of the mallet cube at successive ticks, and a tick is a unit of time in the tangible-graphic interactive game.

7. The method of claim 1 wherein total directional change of a path comprises the sum of the angles between displacement vectors and wherein the total directional change is indicative of a hyperactive patient.

8. The method of claim 1 wherein the average velocity of movement is indicative of inattention.

9. The method of claim 8 wherein the average velocity of movement is the length of the displacement vector divided by the time it took between ticks.

10. The method of claim 1 wherein the game employs spatial, audio and image distractors.

11. The method of claim 7 wherein the directional change is a measure of the angle between displacement vectors at successive ticks.

\* \* \* \* \*